United States Patent [19]
Peters et al.

[11] Patent Number: 5,073,857
[45] Date of Patent: Dec. 17, 1991

[54] METHOD AND APPARATUS FOR CELL ANALYSIS

[75] Inventors: Richard K. Peters; Donald V. Elmerick, both of Tallmadge; James L. Spayer, Brecksville; Gerald E. Walter, Cleveland, all of Ohio

[73] Assignee: Accuron Corporation, Cleveland, Ohio

[21] Appl. No.: 399,824

[22] Filed: Aug. 28, 1989
(Under 37 CFR 1.47)

Related U.S. Application Data

[63] Continuation-in-part of Ser. No. 360,221, Jun. 1, 1989.

[51] Int. Cl.⁵ ............................ G06F 7/38; G06K 1/00
[52] U.S. Cl. .................................. 364/413.1; 358/107; 382/6
[58] Field of Search ......................... 364/413.1, 413.08; 382/6; 358/107, 93; 356/39

[56] References Cited

U.S. PATENT DOCUMENTS

| | | | |
|---|---|---|---|
| 2,965,703 | 12/1960 | Loughlin | 356/526 |
| 3,804,531 | 4/1974 | Kosaka et al. | 356/176 |
| 3,916,176 | 10/1975 | Alien et al. | 364/413.1 |
| 3,935,436 | 1/1976 | Holschlag | 356/96 |
| 3,999,047 | 12/1976 | Green | 382/6 |
| 4,029,419 | 6/1977 | Schumann, Jr. et al. | 356/173 |
| 4,045,655 | 8/1977 | Suzuki et al. | 364/413.1 |
| 4,122,518 | 10/1978 | Castleman et al. | 364/413.1 |
| 4,175,860 | 11/1979 | Bacus | 356/39 |
| 4,213,046 | 7/1980 | Kopp et al. | 364/413.1 |
| 4,253,766 | 3/1981 | Funk | 356/418 |
| 4,402,611 | 9/1983 | Yuasa | 356/405 |
| 4,412,744 | 11/1983 | Lee et al. | 356/319 |
| 4,420,742 | 12/1983 | Tadauchi et al. | 358/464 |
| 4,464,054 | 8/1984 | Karras et al. | 356/406 |
| 4,491,962 | 1/1985 | Sakou et al. | 382/50 |
| 4,505,589 | 3/1985 | Ott et al. | 356/402 |
| 4,518,258 | 5/1985 | Broersma | 356/405 |
| 4,527,897 | 7/1985 | Okabe | 356/407 |
| 4,539,647 | 9/1985 | Kaneko et al. | 364/526 |
| 4,550,435 | 10/1985 | Hayman | 382/9 |
| 4,578,711 | 3/1986 | White et al. | 358/464 |

(List continued on next page.)

FOREIGN PATENT DOCUMENTS 0211272 12/1983 Japan .
0223868 12/1983 Japan .

OTHER PUBLICATIONS

"Introducing Quantitative Imaging Diagnostics", Cell Analysis System/Product Specification 1985.
Pages 886-892 (copy) of article entitled-Automated screening of cervical smears using immunocytochemical staining: a possible approach.
Pages 241-254 (copy) from Gynecologic Oncology-article is entitled-Automated Quantitative Fluorescent Image Analysis of Cervical Cytology.
7 pages of article entitled-Image analysis combined with quantitative cytochemistry.

*Primary Examiner*—Gail O. Hayes
*Attorney, Agent, or Firm*—Henderson & Sturm

[57] ABSTRACT

A pap smear inspection apparatus and method for automated screening of cytological smears for dense, possibly malignant cells includes a specimen slide for receiving a cytological smear and a microscope for enlarging the image of the smear. The microscope is outfitted to receive a video camera for creating an analog video signal corresponding to an area enlarged by the microscope and being observed by the video camea. A video timer synchronizes operation of the smear analysis apparatus. An image window generator focuses the analysis of the apparatus on a sub-area of the entire video image. A converter is provided for converting a digital threshold level into a corresponding analog threshold level. A comparator is used for transforming the analog video input signal into a binary video signal according to the analog threshold levels. A pixel counter sums the number of ON pixels both in the transformed video signal, and within the designated window sub-area of said video signal. A microprocessor compares the digital count output with a user-defined limit on the number of ON pixels allowed to occur within each sub-area under study, and if the limit it exceeded, the current area has failed the test for acceptability.

19 Claims, 3 Drawing Sheets

U.S. PATENT DOCUMENTS

| | | | |
|---|---|---|---|
| 4,581,762 | 4/1986 | Lapidus et al. | 382/8 |
| 4,583,858 | 4/1986 | Lebling et al. | 356/402 |
| 4,592,089 | 5/1986 | Hartman | 358/107 |
| 4,596,037 | 6/1986 | Bouchard et al. | 382/8 |
| 4,635,213 | 1/1987 | Murata et al. | 364/526 |
| 4,653,014 | 3/1987 | Mikami et al. | 364/526 |
| 4,672,559 | 6/1987 | Jansson et al. | 364/525 |
| 4,678,338 | 7/1987 | Kitta et al. | 356/402 |
| 4,692,481 | 9/1987 | Kelly | 356/402 |
| 4,707,138 | 11/1987 | Coatney | 356/402 |
| 4,715,715 | 12/1987 | Howarth et al. | 356/402 |
| 4,723,174 | 2/1988 | Nishikawa et al. | 358/464 |
| 4,736,441 | 4/1988 | Hirose et al. | 382/48 |
| 4,741,043 | 4/1988 | Bacus | 364/413.13 |
| 4,776,024 | 10/1988 | Katoh et al. | 382/9 |
| 4,807,762 | 2/1989 | Illy et al. | 356/425 |
| 4,853,793 | 8/1989 | Ishikawa et al. | 358/464 |
| 4,856,073 | 4/1989 | Farber et al. | 382/6 |
| 4,885,784 | 12/1989 | Miyagawa et al. | 358/464 |
| 4,918,739 | 4/1990 | Lorente et al. | 358/107 |
| 4,959,869 | 9/1990 | Hongo | 382/50 |

METHOD AND APPARATUS FOR CELL ANALYSIS

RELATED APPLICATION

This is a continuation-in-part of U.S. Pat. Application Ser. No. 07/360,221 filed June 1, 1989.

BACKGROUND OF THE INVENTION

I. Field of the Invention

This invention relates to a cytological smear inspection apparatus which may be used to inspect a pap smear specimen for irregular cells.

II. Background of the Invention

Manual inspection of cytological smears, in particular pap smears, involves an extensive number of lab technician man-hours every year. The high volume of such inspections done in many medical laboratories causes delay in their processing. Also, the backlogs which develop due to the high volume contribute to technician fatigue which in turn contributes to technician error. It is this possibility of error coupled with the perpetual backlog that demonstrates the industry need for automated inspection of cytological smears.

The prior art includes a substantial collection of such automated cytological smear inspection constructions—especially such constructions which utilize digital computers; however, the complexity and specialization of the prior art restricts their usage. Specifically, the prior art discloses extensive dedicated machines, obviously requiring enormous amounts of money to produce, yet providing machinery with very limited applications. Obviously, there has been a longstanding need for a cytological smear inspection apparatus which incorporates functionality, affordability, and adaptability, so that an inspection apparatus that works well may be deployed without excessive expense and still be adaptable to inspect a variety of cell types.

SUMMARY OF THE INVENTION

The present invention relates to a pap smear inspection apparatus and method for automated screening of cytological smears for dense, possibly malignant cells. A specimen slide is provided for receiving a cytological smear. A microscope is provided for enlarging the image of the smear. The microscope is further provided with a mechanical stage having the ability to be controlled externally, specifically by an external computer. In addition, the microscope is outfitted to receive a video camera for creating an analog video input signal corresponding to an area enlarged by the microscope and being observed by the video camera. A video timer synchronizes operation of the smear analysis apparatus. An image window generator focuses the analysis of the apparatus on a sub-area of the entire video image; the size of the sub-area is adjusted to maximize recognition of cancerous cells. A digital-to-analog converter is also provided for converting a digital threshold level into a corresponding analog threshold level, wherein both an upper and a lower threshold level may be produced for use. A comparator is used for transforming the analog video input signal into a binary video signal (having only ON or OFF pixels) according to the analog threshold levels, wherein the gray level of the video input must fall between the lower threshold level and the upper threshold level for a pixel to be transformed into an ON state. The thresholds are set so that the extra dense or irregular cells cause a sufficient number of pixels to be activated to facilitate recognition, but also so that normal cells activate few enough pixels that they will not be mistaken for irregular cells.

A pixel counter sums the number of ON pixels in the transformed video signal, but only within the designated window sub-area of said video signal, and produces a digital count output (in binary numerical form) corresponding to the number of ON pixels. A microprocessor compares said digital count output with a user-defined limit on the number of ON pixels allowed to occur within each sub-area under study, and if the limit is exceeded, the current area has failed the test for acceptability. The count will exceed the limit when the cell or cells in the image window are extra dense and possibly cancerous.

A computer program controls operation of the microprocessor, and typically includes computer code to sum the total number of cells present on a slide, as well as code to store and recall the X-Y coordinates of the failed areas of the slide.

A second microscope may be provided along with a second stage and specimen, a second video camera, a second comparator, a second pixel counter, and a second image window generator. A control toggle with associated analog switch allows for alternating between the pair of camera inputs.

An object of the present invention is to provide an improved method and apparatus for inspection of cytological smears.

Another object of the present invention is to provide a method and apparatus of the aforementioned type which includes the capability of having two microscopes, each with a video camera, and of handling two input video signals.

A still further object of the present invention is to allow accurate recognition of obviously benign pap smears so as to reduce the workload of cytologists to inspecting smears of questionable content.

Other objects, advantages, and novel features of the invention will become apparent from the following detailed description of the invention when considered in conjunction with the accompanying drawings.

BEST MODE FOR CARRYING OUT THE INVENTION

Figure 1:
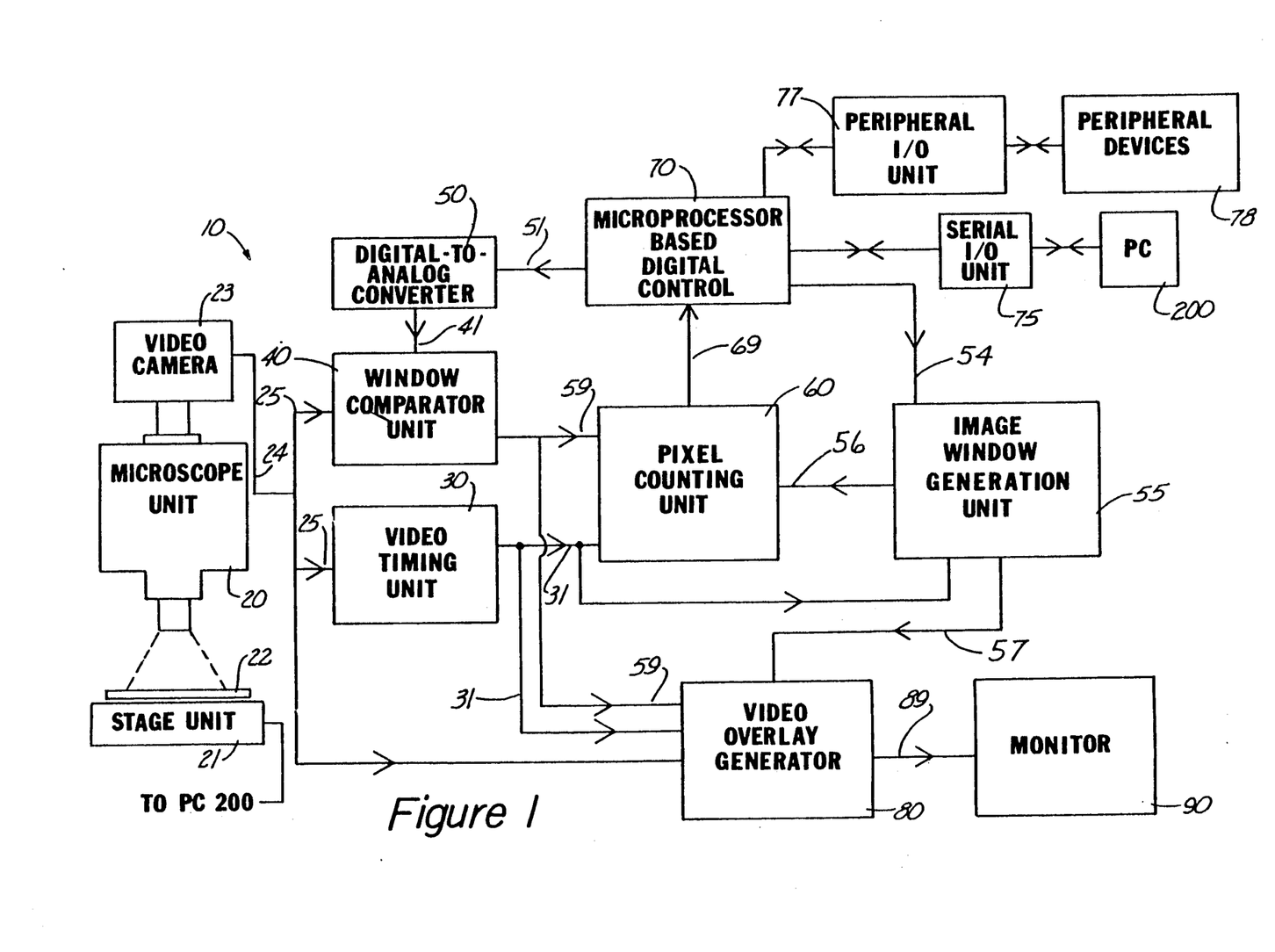
FIG. 1 is a schematic diagram of the cytological smear inspection apparatus.

Referring now to the drawings wherein like reference numerals designate identical or corresponding parts throughout the several views, FIG. 1 shows a pap smear inspection apparatus (10) constructed in accordance with the present invention.

A microscope (20) has a mechanized stage (21) upon which may be placed a specimen slide (22). The microscope (20) is provided with a video camera (23) which has an analog signal output (24) representative of the specimen under observation through the microscope (20).

The analog signal output (24) constitutes an input into a video timing unit (30) and a comparator unit (40). The video timing unit (30) is provided to synchronize the operation of various functions of the apparatus (10). The comparator unit (40) is provided for transforming the video input signal (24) into a binary output signal (59) representative of the video image seen by the camera (23) through the microscope (20). A digital-to-analog converter (50) is utilized to transform digital threshold level inputs (51) into analog threshold level outputs (41) for use by the comparator unit (40).

An image window generator unit (55) focuses the inspection of the apparatus (10) on a desirable sub-area of the entire video image represented by the signal (24). The location and size of this sub-area are controlled by the user and are manipulated so that only a small number of cells may fit into the "window" at any one time.

A pixel counter (60) is employed to count the occurrence of ON pixels within the image window in the binary output (59). A microprocessor based digital control configuration (70) receives the output (69) of the pixel counting unit (60), and the microprocessor configuration (70) analyzes the count output (69) to determine if the current cells under observation fall below a desirable density threshold.

The microprocessor configuration (70) is further utilized to set acceptable ranges for gray levels for the window comparator unit (40) through use of the microprocessor output lines (51) and the digital-to-analog converter (50). The microprocessor is also afforded control of the window generation unit (55) through its output lines (54). In general, the microprocessor configuration (70) is provided with a computer program to lead the microprocessor through the various steps of its operation and analysis.

A video overlay unit (80) highlights the area of the input video image which is currently under inspection by altering the darkness of pixels within that area, and it further alters the pixels within that area which are ON in the binary representation. This overlay unit (80) illustrates to a user the area under analysis as well as the portions binarized by the current set of threshold gray levels.

A personal computer (200) is associated with the smear inspection apparatus (10) and serves to externally access the microprocessor configuration (70) as well as to control the mechanized stage (21) of the microscope (20). The personal computer (200) is further utilized to store the coordinate stage locations of failed cell areas and it may perform other functions such as totaling the number of cell occurrences. The personal computer (200) includes a computer program to control its operation.

The microscope unit (20) of the inspection apparatus comprises an optical instrument which facilitates the magnification of an object from approximately 400 to 1000 times; such a construction is well known in the prior art.

In general, a cytological smear is stained and then spread onto a specimen slide (22) for observation through the microscope unit (20). The slide (22) is placed on a stage unit (21) which is associated with the microscope unit; wherein, movement of the slide (22) by the stage unit (21) causes the portion of the specimen visible through the microscope (20) to change according to the movement.

The stage (21) of the present construction is configured to allow precise control of its capitalize displacement. The stage unit (21) generally includes a stage controller to interface with an external computing device to control stage displacement. The stage unit (21) may be interfaced in general with any computing device, whether it be a standard microprocessor configuration or an independent personal computer. This mechanical stage adjusting mechanism and control can be constructed such as shown in either U.S. Pat. No. 4,700,298 or 4,362,386, which are incorporated herein by reference.

The microscope (20) is further provided with an attachment port (26) at which may be attached a video camera unit (23) such that the enlarged image of the specimen (not shown) produced by the microscope (20) will be introduced into the input of the video camera (23). The video camera (23) creates an analog output signal (24) which is representative of the enlarged image. This output signal (24) serves as the video input signal (25) to the inspection circuitry.

The video input signal (25) includes standard timing signals for horizontal and vertical synchronization of the incoming video signal (25), and referring to FIG. 1, it should be appreciated that the video timing unit (30) receives the horizontal synchronization and the vertical synchronization signals (25). These synchronization signals (25) are then output as synchronization signals (31) to those portions of the smear inspection apparatus (10) which utilize such synchronization information, such as the pixel counter unit (60) and the video overlay unit (80), and the image window generator unit (55).

The image window generator unit (55) serves to reduce the area of the input analog video signal which actually undergoes analysis. The analysis process is focused on a sub-area of the entire video image. The size and location of the sub-area is controlled by the user through the use of the microprocessor control configuration (70) and/or an external computing device.

Figure 2:
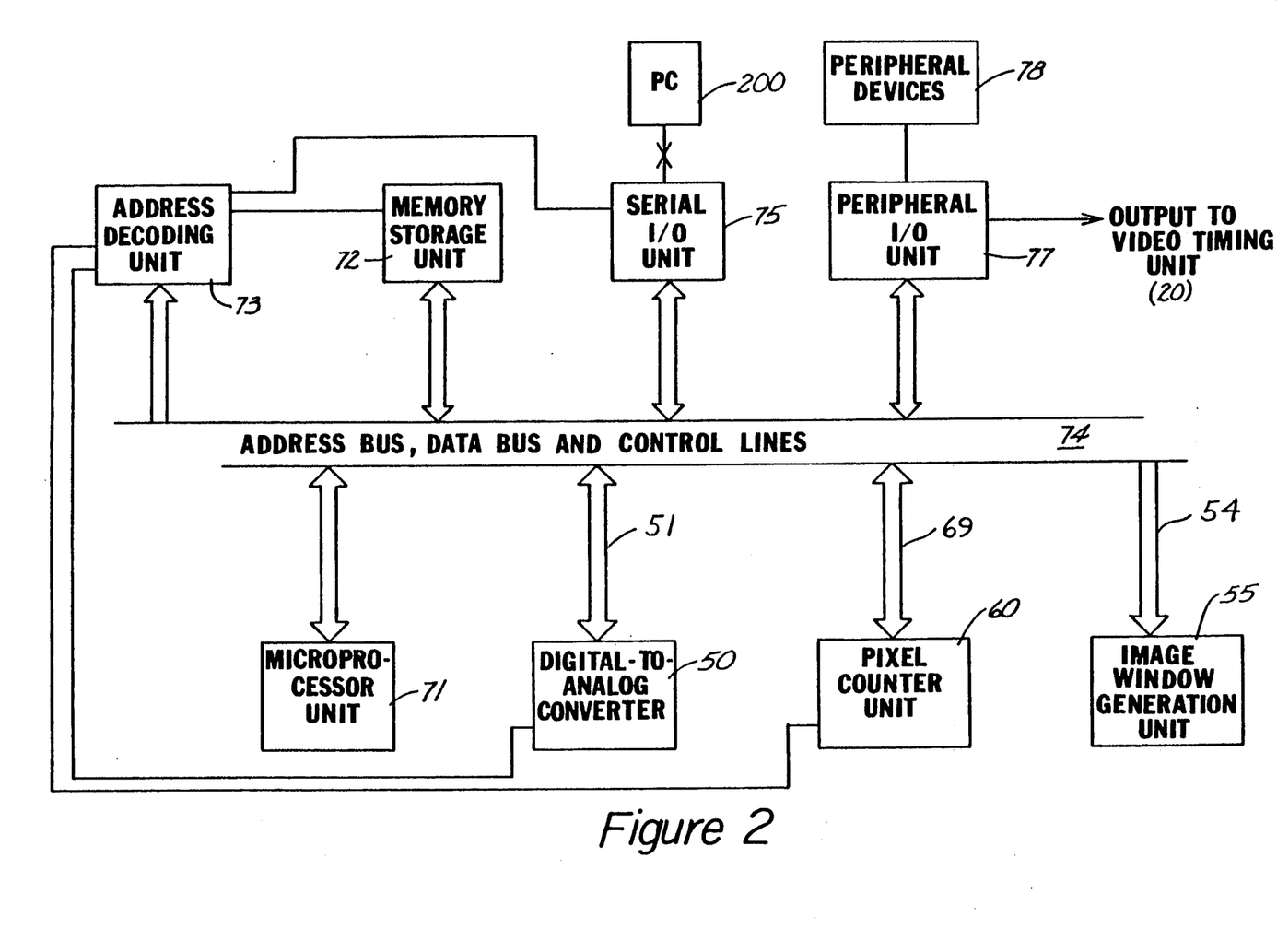
FIG. 2 is a schematic diagram showing the microprocessor control configuration; and, FIG. 3 is a schematic diagram of an alternate embodiment of the cytological smear inspection apparatus.

Typically, the size and location of the image window, or sub-area, is input to an external personal computer (200) which transfers such information to the resident microprocessor control configuration (70) which oversees implementation of the image window through its control and information lines (54) connected to the window generation unit (55), as shown in FIG. 1 and FIG. 2.

The size is the most important aspect of user control. It is typically adjusted so that only a few regular cells or a single irregular cell will fit within the generated window. This control, coupled with the feedback of the video overlay unit (80), which will be discussed in detail later in this specification, form the basis for the cell recognition ability of the present embodiment.

Still referring to FIG. 1, the comparator unit (40) of the inspection apparatus (10) is a voltage comparator configuration which receives an analog video input signal (25) and an analog threshold voltage. The threshold voltage includes a lower analog threshold voltage which is provided by the digital-to-analog converter (50) through the comparator input lines (41).

The comparator unit (40) determines if the gray level of the input signal (25) exceeds the lower threshold. If the current pixel's voltage does exceed the threshold, then the output (59) of the comparator (40) will indicate that the current pixel is ON. Otherwise, the comparator will output a low voltage-indicative of an OFF pixel.

The comparator unit (40) may alternately comprise a window comparator; wherein, the window comparator (40) receives both an upper threshold and a lower threshold from the digital-to-analog converter unit (50). In this embodiment, the current pixel's voltage (or gray level) must fall between the threshold levels for the pixel to be transformed into a binary ON state. This embodiment allows the user to exercise further control over the transformation of the input signal.

The digital-to-analog converter (50) of FIG. 1 comprises a standard D/A converter; in this configuration, the converter (50) receives digital information from the microprocessor based digital control configuration (70) through input lines (51) and outputs analog voltages to the comparator unit (40) on output lines (41).

In general, the digital information (51) to the D/A converter (50) from the microprocessor configuration (70) includes the digital gray level representation of an upper or lower threshold as well as information to indicate which threshold is currently being provided. The converter (50) then provides the analog threshold to the appropriate threshold input of the comparator unit (40).

Still referring to FIG. 1, it may be appreciated that the pixel counting unit (60) provides a way to count the occurrences of ON pixels from the comparator unit (40) in the binary signal output (59). The output count (69) of the pixel counting unit (60) is accepted by the microprocessor control configuration (70). The pixel count output (69) is, in general, provided to the microprocessor configuration (70) at the end of each horizontal line of the binary signal (59). However, the counter arrangement may vary so that the count will be provided at any desired interval to the microprocessor (70), such as at the end of an entire frame.

The pixel counting unit (60) further receives an input signal (31) from the video timing unit (30). This input signal (31) serves to synchronize the counting unit (60) with the video input (25) such that the pixel count conforms to the desired counting interval, whether that interval be one horizontal line or one entire frame. The counting unit (60) receives another input signal (56) from the image window generator (55) to insure that counting only occurs within the image sub-area designated by the generator unit (55). (This is generally implemented through use of logic circuitry).

Turning now to FIG. 2, the microprocessor based digital control configuration (70) includes a microprocessor unit (71) for performing the required control and analysis operations of the smear inspection apparatus (10) of FIG. 1. As is well known, the control and analysis operations are put into a computer program form which controls the microprocessor unit (71), and the microprocessor unit (71) in turn uses this program to function as the controlling force for the apparatus (10).

A memory storage configuration (72) is utilized to store said computer program, as well as any data pertinent to the desired analysis. In general, the memory storage unit will include a combination of random access memory (RAM) units and read only memory (ROM) units.

The address decoding unit (73) is employed to multiplex the address lines into control lines for signalling a device that it should send or receive information on the data bus (74). In general, the address decoding unit (73) will send control signals to the individual memory units, the serial input/output unit (75), the digital-to-analog converter unit (50), and the pixel counter unit (60).

The serial input/output unit (75) of the microprocessor configuration (70) comprises a standard serial data interchange configuration such that data may be serially received to or transmitted from the microprocessor unit (71). Typically, a standard RS-232 serial port or RS-422 port is utilized for the interchange of data. This serial data exchange unit (75) is provided to allow an independent personal computer (200) or similar external computing device access the microprocessor unit (71). In this way, the characteristics controlling operation of the smear inspection apparatus (10) may be controlled and programmed into the apparatus (10) through the use of external computing devices. The smear inspection apparatus (10) may utilize the external personal computer (200) to control the mechanized stage (21) of the microscope (20), to record X-Y coordinate stage locations of areas which fail the inspection and thus require human examination, to sum the occurrences of cells to insure adequate sample size, as well as to program the other functions discussed above.

The microprocessor configuration (70) may include a peripheral input/output unit (77) to facilitate the interchange of signals and information as needed with external peripheral devices (78).

In general, an object of interest in a video picture fills much less than the entire video area, thus the image window generation unit (55) is provided in this embodiment of the smear inspection apparatus (10). The image window generation unit (55) allows the analysis to be limited to a sub-area of the entire video picture. In this way, only the sub-area of direct and significant importance is analyzed, thus allowing greater flexibility in the description of the analysis requirements.

The image window generation unit (55) receives an input (54) from the microprocessor configuration (70). This input (45) permits the microprocessor unit (71) to control the size and location of the image window. The desired size and location information are provided to the generation unit (55), which in turn uses those parameters and a series of timing mechanisms to generate the appropriate signals to the counter unit (60) and the video overlay unit (80) such that only transformed pixels within the image window will be summed and such that only pixels within the image window will be offset in any way at the video output (89). In this way, the analysis is effectively limited to the desired sub-area and the output video will clearly show the sub-area and the binary transformation within that sub-area, thus serving as a powerful feedback tool for the system operator.

Returning now to FIG. 1, the video overlay unit (80) is provided to produce an especially useful output form of the input video signal (25). The video overlay unit (80) receives the input video signal (25) from the video camera unit (23), as well as an input (59) from the comparator unit (40), an input (31), from the video timing unit (30) and an input (57) from the image window generation unit (55). The output (89) of the video overlay unit (80) is a standard video signal having various pixels modified; the output (89) will in general be provided to a monitor unit (90) for display of the output video signal (89).

The video overlay unit (80) operates in such a fashion that all pixels subjected to the binary transformation scheme, i.e. those within the image window sub-area, will be slightly altered. This alteration is different for ON pixels than for OFF pixels. The video overlay output unit (80) produces this alteration by applying an offset voltage to the pixels which are undergoing gray level analysis and binary transformation. This offset voltage will, in general, increase the gray level of the pixel and thus highlight the pixel. If the pixel is found to be ON in the binary transformation, the offset will be greater than if it is found to be OFF. In this way, the ON pixels will be darker pixels and this altered display may be used as a feedback mechanism by the operator in setting the appropriate threshold levels so that the dense cells, which are of particular interest, activate enough pixels so as to differentiate themselves from ordinary cells. In this way, the count output (69) for each window sub-area will be indicative of the presence of dense cells versus regular cells.

The monitor unit (90) utilized to display the output video signal (89) is a standard television monitor which will accept a standard video signal as an input, and which will output that signal in a visually recognizable form.

Figure 3:
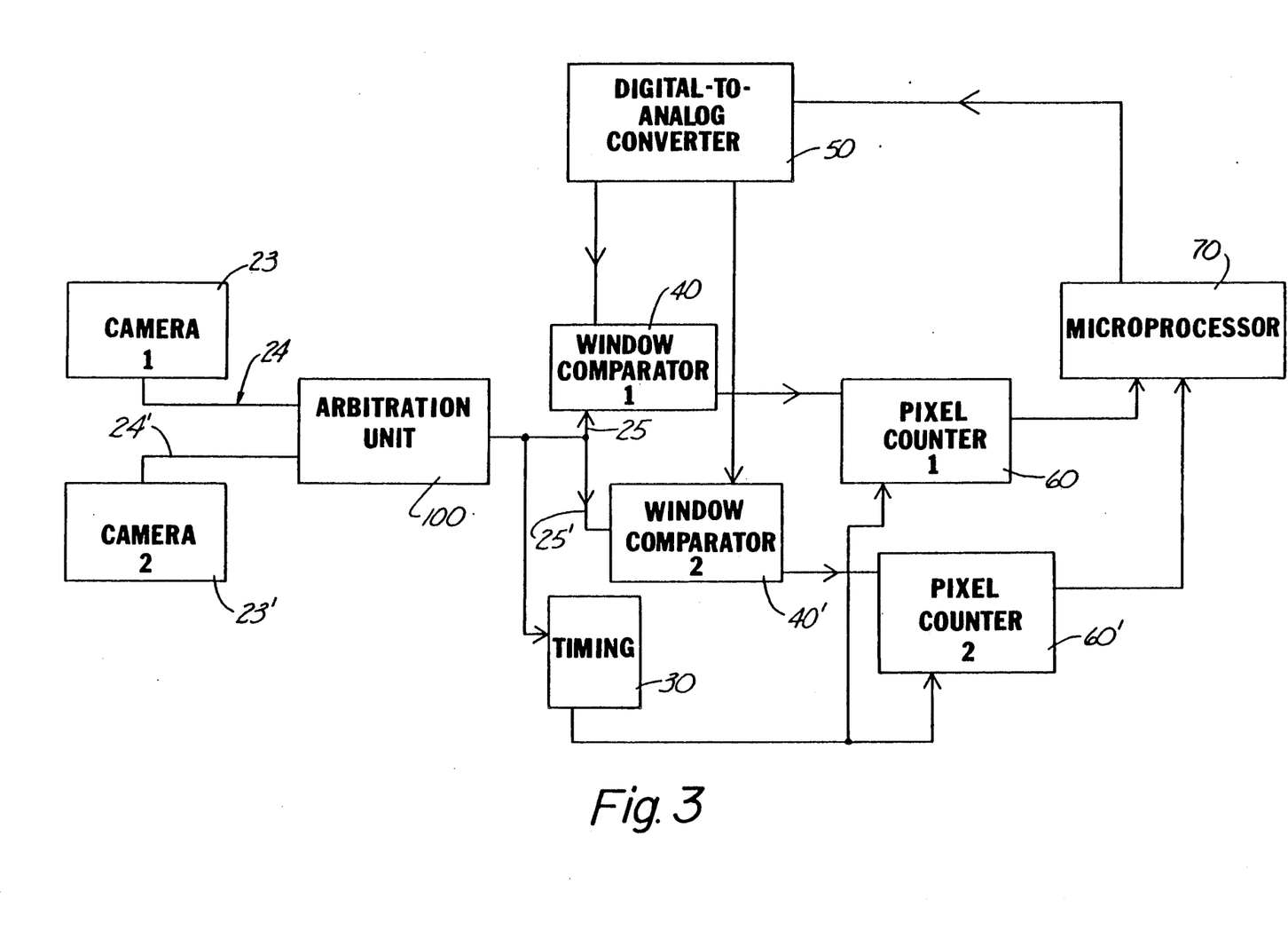

In the alternate embodiment of the present invention as shown in FIG. 3, the smear inspection apparatus (10) will include a second cytological smear on a second specimen slide (22'), a second microscope unit (20'), a second video camera (23') having an associated second analog signal output (24')just like the camera (23) and video camera arrangement in FIG. 1. In addition, an arbitration unit (100) will be utilized to produce a control toggle signal to control which camera output is to be analyzed.

A second comparator unit (40') is provided for transforming the second input signal (25') based on distinct threshold levels set by the microprocessor (70). The toggle signal controls an analog switch which alternates passing the video camera one output (25) and the video camera two output (25') to the associated comparator unit (40) or (40') for transforming the signal into binary form. The digital-to analog converter (50) is configured so as to provide thresholds for the first comparator (40) as well as the distinct thresholds for the second comparator (40') as needed by the respective comparator units (40) and (40').

Further, a second pixel counting unit (60') identical to the first pixel counting unit (60) except that the second counter (60') counts the active pixels as transformed by the second comparator (40'). Just as in the case of single camera operation, the output of the second pixel counter (60') is routed to the microprocessor control unit (70) for analysis of the second specimen.

Accordingly, it will be appreciated that the preferred embodiment disclosed herein does indeed accomplish the aforementioned objectives. Obviously, many modifications and variations of the present invention are possible in light of the above teachings. It is therefore to be understood that, within the scope of the appended claims, the invention may be practiced otherwise than as specifically described.

We claim:

1. A method of cell analysis for a smear inspection apparatus having: a cytological smear, a specimen slide, a microscope including a video camera mounting, a mechanized microscope stage, a video input provided by a video camera mounted on said video camera mounting, a video timing unit, a non-magnifying image window generator, a digital-to-analog converter, a comparator, a pixel counter, a microprocessor control, a computer program for the microprocessor, and an external computing device having an associated computer program, said method comprising:

choosing an appropriate sub-area of an image represented by said video input through the use of said non-magnifying image window generator, wherein, the image window generator serves no magnification function, but merely limits the analysis to that area within the chosen window;

transforming said input video signal into a binary form by comparing the gray level of said input signal to a threshold level in analog form, wherein the threshold level is produced in analog form from a digital gray level through the use of said digital-to-analog converter;

summing the ON pixels along one horizontal line within said image sub-area of the binary signal and then outputting said sum to said microprocessor control;

summing the total number of ON pixels within entire said image sub-area by adding the output after each line to the ongoing total;

comparing total number of ON pixels with a predetermined limit, wherein, the current sub-area will fail the inspection if the total exceeds said limit; and, moving said mechanized microscope stage mechanically and systematically so that the analysis is done in increments to cover the entire area of said specimen wherein, the movement of the specimen slide occurs in a programmed and sequential fashion under control of said external computer device and its associated computer program, and wherein, the increment size by which the stage is displaced corresponds generally to the size of the image window.

2. A method of cell analysis for a smear inspection apparatus having: a cytological smear, a specimen slide, a microscope including a video camera mounting, a mechanized microscope stage, a video input provided by a video camera mounted on said video camera mounting, a video timing unit, a non-magnifying image window generator, a digital-to-analog converter, a comparator, a pixel counter, a microprocessor control, a computer program for the microprocessor, and an external computing device having an associated computer program, said method comprising:

choosening an appropriate sub-area of an image represented by said video input through the use of said non-magnifying image window generator, wherein, the image window generator serves no magnification function, but merely limits the analysis to that area within the chosen window;

transforming said input video signal into a binary form by comparing the gray level of said input signal to a threshold level in analog form, wherein the threshold level is produced in analog form from a digital gray level through the use of said digital-to-analog converter;

summing the total number of ON pixels within the entire image window sub-area through the use of said pixel counter and then outputting the end total to said microprocessor control;

comparing total number of ON pixels with a predetermined limit, wherein, the current sub-area will fail the inspection if the total exceeds said limit; and, moving said mechanized microscope stage mechanically and systematically so that the analysis is done in increments to cover the entire area of said specimen wherein, the movement of the specimen slide occurs in a programmed and sequential fashion under control of said external computing device and its associated computer program, and wherein, the increment size by which the stage is displaced corresponds generally to the size of the image window.

3. A pap smear inspection apparatus for automated screening of cytological smears, said inspection apparatus comprising:
 a slide for holding a cytological smear;
 microscope means for producing an enlarged image of at least a portion of the smear;
 mechanized stage means for holding said slide;
 stage control means for facilitating automated external control of stage displacement;
 video camera means for creating an analog video input signal, comprised of pixels, corresponding to at least a portion of said enlarged image produced by said microscope means;
 non-magnifying image window generator means for focusing analysis of the apparatus on a sub-area of the entire video image, wherein means are included for permitting the user to adjust the size of the sub-area to maximize recognition of cancerous cells;
 digital-to-analog converter means for converting a digital threshold level into a corresponding analog threshold level;
 comparator means for transforming the analog video input signal into a binary video signal according to the analog threshold level, wherein the gray level of the current pixel of said video input signal must be greater than said analog threshold level for said pixel to be transformed into an ON state;
 pixel counter means for summing the number of ON pixels in said binary video signal within the designated window sub-area of said video signal thereby producing a count output corresponding to said number of ON pixels;
 video timer means for synchronizing the pixel counting and the image window generator means with the input video signal;
 microprocessor control means for controlling operation of the apparatus said microprocessor including means for providing said image window size and location information to the non-magnifying image window generator means, means for providing the digital threshold level to said d-to-a converter means, means for comparing said count output with a predetermined limit on the number of ON pixels allowed to occur within any sub-area under study, and means for indicating a failure if the count is exceeded; and
 computer program means for controlling the operation of the microprocessor control means.

4. The apparatus of claim 3 wherein the comparator means includes a window comparator means for transforming the analog video input signal into a binary video signal by utilizing an upper threshold level and a lower threshold level, both received from the d-to-a converter means, wherein said gray level of the current pixel must be greater than the lower threshold level and less than the upper threshold level for said current pixel to be transformed into an ON state.

5. The apparatus of claim 3 or 4 wherein the inspection apparatus further comprises:
 external computing means connected to the microprocessor control means and to the stage control means for adjusting the position of said stage means, wherein the external computing means and the microprocessor control means include means which allow the setting of the size and location of the image window from the external computing means, means which allow the choosing of the threshold levels from the external computing means, and/or means which coordinate the movement of the stage with the size and location of the image window sub-area; and
 program control means for controlling said external computing means.

6. The apparatus of claim 3, 4 or 5 wherein the microprocessor control means comprises:
 microprocessor unit for controlling operation of the inspection apparatus;
 computer program for providing instructions in machine readable form to the microprocessor unit;
 memory storage means for storing information for use in the microprocessor unit;
 address decoding means for facilitating access by the microprocessor unit to other portions of the apparatus;
 serial input/output means for facilitating the serial exchange of input and/or output between the microprocessor unit and external computing means; and
 peripheral input/output means for communication of input and/or output between the microprocessor unit and external peripheral devices.

7. The method of claim 1 or 2 further comprising the choosing of the size and location of said image window sub-area through the use of said external computing device.

8. The method claim of claim 7 further comprising a video overlay unit and a video output unit, and further involving the use of said video overlay unit as a feedback mechanism so that the input video signal is shown on the video output unit, wherein the video overlap unit high-lights the image window sub-area while the remainder of the image remains at its normal intensity, and wherein the pixels within said sub-area which are turned ON by the comparator are further high-lighted; whereby, a user may have visual feedback to see the chosen sub-area and the affect the threshold settings have on the video input and may see exactly which cells are activated by the current threshold settings.

9. A smear inspection apparatus for automatically checking a pap smear for specified characteristics, said inspection apparatus comprising:
 a slide for holding a cytological smear;
 microscope means for producing an enlarged image of the smear;
 mechanized stage means for holding and moving said slide;
 stage control means for facilitating automated control of the displacement of said mechanized stage means;
 video camera means for creating an analog video signal corresponding to the magnified image produced by said microscope means;
 non-magnifying image window generation means for isolating a sub-area of the total image area being observed by the video camera means and for producing control signals such that analysis will occur only within the image window sub-area;
 a digital-to-analog converter means for converting a digital threshold gray level into an analog threshold level corresponding to said digital threshold level, where an upper and a lower threshold level are produced;
 comparator means for transforming said analog video input signal into a binary form based on said analog threshold levels, where the video input gray level must fall between the lower threshold level and the upper threshold level for the pixel to be transformed into a binary ON state;

pixel counting means for summing the number of ON pixels in said binary video signal within the image window sub-area of said video signal and producing a count output corresponding to the number of ON pixels;

video timing means for coordinating synchronous operation of the pixel counting means and the image window generator means with the input video signal;

a microprocessor based digital control means for analyzing and comparing the ON pixel count with expected and desired count results, means for providing sub-area size and location information and control signals to the image window generator, and means for providing said digital threshold gray level to the d-to-a converter;

program means for controlling operation of said microprocessor means; and, a serial input/output means associated with said microprocessor based digital control means for communicating input and/or output with an external computing device.

10. The apparatus of claim 9 wherein the external computing device includes means for setting the size and location of the image window sub-area, means for communicating with and thereby controlling said stage control means, and means for generally coordinating the movement of the stage with the image window size and location so that the mechanized stage is displaced mechanically and systematically so as to incrementally bring the entire area of said specimen within the image window sub-area.

11. The apparatus of claim 9 or 10 wherein the microprocessor based digital control means includes a peripheral input/output means for communicating input and/or output with an array of peripheral devices.

12. The apparatus of claim 9 wherein the pap smear inspection apparatus further comprises:

a second cytological smear associated with a second specimen slide;

a second microscope means for producing an enlarged image of said second smear;

a second mechanized stage means for holding and moving said second specimen slide;

a second stage control means for facilitating automated control of the displacement of said second mechanized stage means;

a second video camera means for creating a second analog video input signal, said second video signal corresponding to the enlarged image produced by the second microscope means;

said digital-to-analog converter including means for providing a second set of analog threshold levels to a second comparator means;

arbitration means for switching between said first and said second video input signals;

a second comparator means for transforming said second analog video input signal into a second binary video signal based on said second analog threshold gray levels, where said second video input pixel gray level must fall between the second lower threshold level and the second upper threshold level for the pixel to be transformed into an ON state;

a second pixel counting means for summing the number of ON pixels in said second transformed video signal within a predetermined portion of said second video signal and for producing a count output corresponding to said number of ON pixels, wherein said predetermined portion is a sub-area selected through use of the non-magnifying window generation means, and wherein said sub-area for the second video signal may be independent of the sub-area chosen for said first video signal; and said non-magnifying image window generation means including means for choosing a sub-area of the total image area being observed by the first or second video camera means and means for producing control signals such that the summing of ON pixels will occur only over that area within said non-magnified image window; said microprocessor based digital control including means for analyzing and comparing said second digital count output as well as said first digital count output with expected and desired count results, where said expected count result for the first count output may be independent of the expected count result for the second count output; and wherein, the microprocessor based digital control further includes means such that the information deriving from said second slide is analyzed in a concurrent, yet independent, fashion with that of said first slide, thereby allowing the single microprocessor based digital control to simultaneously control analysis of two distinct specimen; and, said external computing device including means for choosing sizes and locations for the image window sub-areas, wherein the sub-areas for said first and said second video signals may be independent of one another; means for communicating with and independently controlling said first and said second stage control means; and means for coordinating the first image window sub-area characteristics with the movement of said first stage, and for coordinating movement of the second stage to said second image window sub-area, to cause each mechanized stage to be displaced mechanically and systematically so that incrementally the entire area of each said first and said second specimen slides will be brought within its associated image window sub-area.

13. The apparatus of claim 12 wherein the microprocessor based digital control means includes a peripheral input/output means for communicating input and/or output with an array of peripheral devices.

14. The apparatus of claim 9 wherein the microprocessor based digital control means includes an address decoding means for decoding address lines to produce control signals.

15. The apparatus of claim 9 wherein the microprocessor based control means includes a memory storage means; wherein, the memory storage means includes at least one random access memory means and/or at least one read only memory means.

16. The apparatus of claims 9, 10, 11, 12, 3, 4 or 5 wherein the inspection apparatus further comprises video overlay means for highlighting an area of the output signal corresponding to the image window sub-area of the video input signal as well as further highlighting ON pixels which fall within that window sub-area in the binary video signal, wherein said highlighting is produced by adding an offset voltage to affected pixels, whereby said video overlay means serves to provide a feedback mechanism to the user so that said user may visually see the area chosen by the image window settings and the pixels affected by the threshold settings.

17. The apparatus of claim 16 wherein the inspection apparatus further includes a television monitor means for displaying the output video signal.

18. A pap smear inspection apparatus for automated screening of cytological smears, said inspection apparatus comprising:

a slide for holding a cytological smear;

microscope means for producing an enlarged image of at least a portion of the smear;

mechanized stage means for holding said slide;

stage control means for facilitating external control of stage displacement;

video camera means for creating an analog video input signal, comprised of pixels, corresponding to at least a portion of said enlarged image produced by the microscope;

non-magnifying image window generator means for focusing analysis of the apparatus on a sub-area of the entire video input signal, wherein means are included for allowing a user to adjust the size of the subarea to maximize recognition of cancerous cells;

digital-to-analog converter means for converting a digital threshold level into a corresponding analog threshold level;

comparator means for transforming the analog video input signal into a binary video signal according to the analog threshold level, wherein the gray level of the current pixel of said video input signal must be greater than said analog threshold level for said pixel to be transformed into an ON state;

pixel counter means for summing the number of ON pixels in said binary video signal within the designated window sub-area of said video signal thereby producing a count output corresponding to said number of ON pixels;

microprocessor control means for controlling operation of the apparatus said microprocessor including means for comparing said digital count output with a predetermined limit on the number of ON pixels allowed to occur within any sub-area under study, means for indicating a failure if the limit is exceeded, and means for providing said size and location limitations to the non-magnifying image window generation means; and computer program means for controlling the operation of the microprocessor control means.

19. The apparatus of claim 18 wherein the apparatus further comprises an external computing device which includes means for communicating with said microprocessor control means, means for communicating with and thereby controlling said stage control means, and means for generally coordinating the movement of the stage with the image window size and location so that the mechanized stage is displaced mechanically and systematically so as to incrementally bring the entire area of said specimen within the image window sub-area.

* * * * *